United States Patent [19]

Rautenberg

[11] Patent Number: 4,880,424
[45] Date of Patent: Nov. 14, 1989

[54] PROTECTIVE UNDERGARMENT FOR THE RETENTION OF BODY FLUIDS

[75] Inventor: Leonard J. Rautenberg, Sands Point, N.Y.

[73] Assignee: Darlington Fabrics Corporation, New York, N.Y.

[21] Appl. No.: 152,182

[22] Filed: Feb. 4, 1988

[51] Int. Cl.⁴ ............................................. A61F 13/16
[52] U.S. Cl. ........................................ 604/396; 2/401
[58] Field of Search ................ 604/396, 392, 366; 2/401, 400, 406

[56] References Cited

U.S. PATENT DOCUMENTS

| | | | |
|---|---|---|---|
| 2,664,895 | 1/1954 | Shalman | 604/366 |
| 3,613,686 | 10/1971 | Woshkin | 604/376 |
| 4,022,212 | 5/1977 | Lovison | 604/396 |
| 4,187,390 | 2/1980 | Gore | 428/320.2 |
| 4,244,367 | 1/1981 | Rollenhagen | 604/396 |
| 4,338,938 | 6/1982 | Scavitt | 604/386 |
| 4,352,356 | 10/1982 | Tong | 604/392 |
| 4,411,660 | 10/1983 | Dawn et al. | 604/396 |
| 4,560,381 | 12/1985 | Southwell | 604/396 |
| 4,586,199 | 5/1986 | Birring | 2/401 |
| 4,641,381 | 2/1987 | Heran et al. | 604/392 |
| 4,690,681 | 9/1987 | Haunschild et al. | 604/396 |
| 4,695,279 | 9/1987 | Steer | 604/397 |
| 4,701,171 | 10/1987 | Boland et al. | 604/396 |
| 4,713,069 | 12/1987 | Wong et al. | 604/382 |
| 4,718,902 | 1/1988 | Bonito | 604/396 |
| 4,729,131 | 3/1988 | Thygesen | 2/400 |
| 4,761,324 | 8/1988 | Rautenberg et al. | 428/198 |
| 4,813,950 | 3/1989 | Branch | 604/396 |
| 4,828,556 | 5/1989 | Braun et al. | 604/366 |

Primary Examiner—C. Fred Rosenbaum
Assistant Examiner—Mark O. Polutta
Attorney, Agent, or Firm—Darby & Darby

[57] ABSTRACT

A garment to be worn on the lower part of the body for the retention of body fluids includes a body portion and a crotch portion. The body portion has a waist opening and the body and crotch portion form leg openings. A laminated fabric is disposed at least in the crotch portion for the retention of body fluids. The laminated fabric is liquid-proof, breathable and elastic. A preferred form of the laminated fabric includes a thermoplastic film layer and a fiber-containing material layer. The film layer is disposed inside the garment when the garment is worn.

5 Claims, 1 Drawing Sheet

U.S. Patent
Nov. 14, 1989
4,880,424
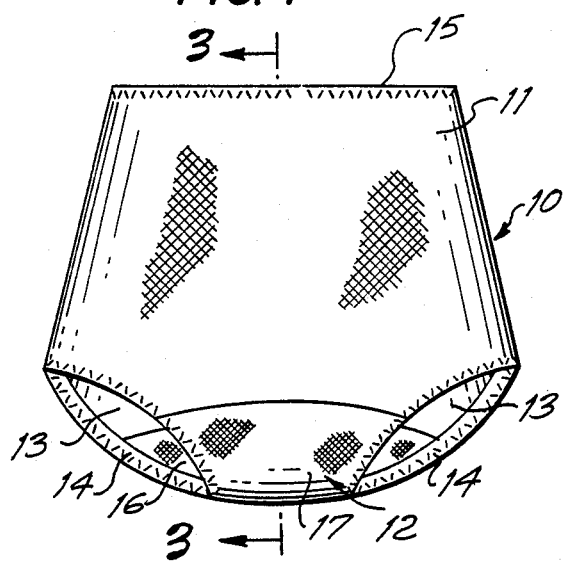
FIG. 1
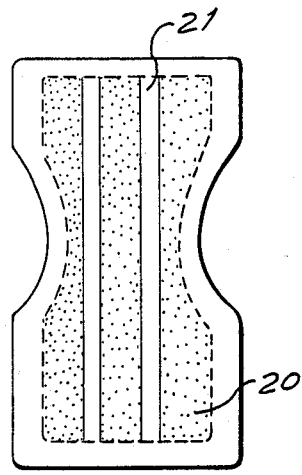
FIG. 2
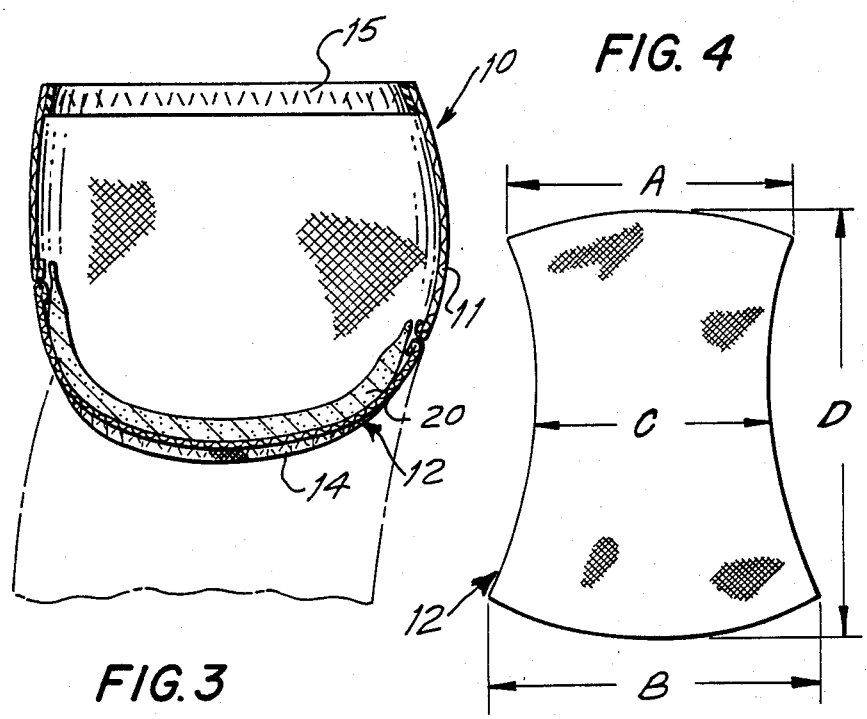
FIG. 3
FIG. 4

PROTECTIVE UNDERGARMENT FOR THE RETENTION OF BODY FLUIDS

FIELD OF THE INVENTION

The present invention relates to protective undergarments and more particularly, to an undergarment which incorporates a liquid-proof or liquid-resistant croth portion.

BACKGROUND OF THE PRESENT INVENTION

Incontinence is a condition of particularly sensitive nature, but should not be a debilitating one. Using a hypothetically perfect optimal garment, the incontinent individual should be able to function normally, comfortably and without constant worry about embarrassing leakage of urine. Garments currently on the market which attempt to solve this problem lack some crucial aspect of comfort-retention balance, namely, they do not afford optimal liquid-retention and comfort to the wearer.

The comfort of the optimal incontinent undergarment includes four aspects: good fit, elasticity, breathability and discreetness. A well-fitting elastic undergarment will stretch adequately to accommodate to the wearer comfortably, yet it clings to the skin sufficiently to maintain fluid retention. Elasticity makes movement easier and more comfortable to the wearer, as well as minimizing garment shifting during significant movement. Breathability indicates a water-vapor transmitting garment enabling the user's body moisture to escape (but at the same time affording protection against escape of liquid if the garment is liquid-proof), as well as promoting hygiene by keeping the crotch area dry. Discreetness is assured by the softness and drape which renders it silent as opposed to a plastic diaper or or non-woven paper diaper which is audible when the user moves. Further, in this regard, the nearer the garment appears outwardly to be an ordinary undergarment (i.e., a woman's elastic brief or panties, for example), the more appealing and discreet the garment is.

The retentive aspect of the optimal incontinent undergarment includes: snugness, liquid penetration-resistance, and adaptability to use with an absorbent crotch pad or pads. Because prior garments of this type were not well fitting, they were not well adapted for use for the related purpose as a retainer of absorbent pads for women's menstrual flow.

Garments on the market typically have one or two of the above features, however, there are none having all of the features required for an optimum protective garment.

It is accordingly an object of the present invention to provide an undergarment, specifically, one to be worn on the lower body for retention of body fluids which is comfortable, well fitting and discreet.

It is also an object of the present invention to provide such an undergarment for retention of body fluids which is liquid-proof, elastic and breathable.

It is another object of the present invention to provide an undergarment for retention of body fluids which is snug, liquid-resistant or liquid-proof and adapted to be used with an absorbent crotch shield.

It is a further object of the present invention to provide an undergarment for retention of body fluids which is durable and does not have a tendency to deteriorate during ordinary use, including machine washing and drying.

It is yet another object of the present invention to provide an undergarment which will accept disposable absorbent shields for women's menstrual flow.

It is to be understood that the terms "stretch" and "elastic" are used interchangeably in this specification.

SUMMARY OF THE INVENTION

In accordance with the invention, a garment is to be worn on the lower part of the body for the retention of body fluids, comprises a body portion and a crotch portion. The body portion has a waist opening and the body portion and crotch portion form leg openings. Means are disposed, at least in the crotch portion, for the retention of body fluids. The means are liquid-proof, breathable and elastic.

In one form of the invention, the means includes a laminated fabric, the fabric including a liquid-proof, breathable elastic thermoplastic film layer and a breathable stretch fiber-containing material layer. The film layer is disposed inside the garment when the garment is worn.

For a better understanding of the present invention, reference is made to the following description and accompanying drawings, while the scope of the present invention will be pointed out in the appended claims.

BRIEF DESCRIPTION OF THE DRAWINGS

In the drawings:

FIG. 1 represents a frontal view of a undergarment in accordance with the invention;

FIG. 2 illustrates an absorptive pad for use with the undergarment of FIG. 1;

FIG. 3 illustrates a side sectional view taken along 3—3 of FIG. 1; and

FIG. 4 represents a plan view of the crotch portion of the undergarment shown in FIG. 1.

DESCRIPTION OF THE PREFERRED EMBODIMENTS

Referring initially to FIG. 1, an undergarment is shown there, 10, with a body portion 11 and a crotch portion 12. The body portion 11 is preferably a spandex fiber-containing stretch fabric, typically knitted, while the crotch portion 12 is composed of a laminate having a fabric similar to the stretch fabric of the body portion 11 on the outside of the crotch area, while a thermoplastic elastic film 16 is disposed in the crotch area on the inside of the garment.

The undergarment contains a waist portion 15 and leg portions 13 having elastic leg bands 14 for improving the liquid retention capabilities of the garment. The waist 15 also includes an elastic band as is typical in this garment.

The garment is designed to enhance both the liquid retention capabilities of the garment, as well as the overall attractiveness. It is specially designed and constructed to provide optimal service for use with an absorptive pad 20 as shown in FIG. 2. The key to the garment is the crotch portion 12. This is constructed especially as a laminate having an outer layer 17 made of a stretch fiber-containing material (preferably a knit material) which is bonded to a thermoplastic stretch film by a suitable adhesive. Such laminate is elastic, breathable and liquid resistant or liquid-proof. A suitable laminate is described in application Ser. No. 068,907, filed June 24, 1987, now U.S. Pat. No.

4,761,324 the disclosure of which is incorporated herein by reference. The laminate described in that application includes a layer of stretch material having substantial elastic qualities and a polymer film having a thickness less than 1.0 mil. The film is breathable and water-resistant and has elastic qualities comparable to the stretch material. For the garment described herein, polyurethane film having an 0.8 mil thickness is preferred.

The pad is a standard absorptive pad, such as made by a company called ICD, under the brand name "SURE-TYS". The crotch area is designed to accommodate the size of the pad and to allow for the best retention/comfort qualities of the garment. FIG. 3 illustrates the disposition of pad 20 in the crotch area of the garment 10 when worn.

The retention capabilities of the leg band, crotch and pad system depend on the use of a properly tensioned leg band. If the leg band is not snug enough, liquid retention will not be at an optimum level. If the band is too tight, discomfort will be caused to the wearer.

The making of the garment requires special attention in that fabrics of two different types are used in the crotch and body portions. Certain parts of the garment require shirring, particularly in the crotch area. Because of the unusual characteristics of the laminated fabric used in the crotch, special ballpoint needles must be used to prevent cutting of the laminate, maintain uniform stitch size and reduce thread breakage. The machines used in sewing the garment must be run at speeds substantially below that used in conventional manufacturing procedures.

Three different types of threads are used in the garment: (1) regular nylon thread for additional strength; (2) stretch nylon thread for stretchability as well as strength and softness; and (3) polyester thread for durability.

Further, all machine feeder plates and presser feeds must be specially TEFLON ® coated in order to join the laminated fabric of the crotch portion with the conventional nylon/spandex of the body portion.

In addition to providing the liquid retention capability to the crotch area, the film layer of the laminate also acts as a more secure place to fasten the underside of the shield, which ordinarily contains an adhesive strip (not shown). This prevents sliding of the shield when being worn.

on, the garment is made in three sizes designated medium, large/extra large, and 2x/3x. The various preferred dimensions of these garments are as follows:

| (a) Leg openings | medium - 8 inches |
| | large/extra large - 8½ inches |
| | 2x/3x - 9 inches |
| (b) Side seam | medium - 9¼ inches |
| | large/extra large - 9½ inches |
| | 2x/3x - 10¼ inches |
| (c) Waist | medium - 11 inches |
| | large/extra large - 12 inches |
| | 2x/3x - 13 inches |

The crotch is usually the same for all three sizes. From front to back, designated "D" in FIG. 4, the preferred dimension is 11¼ inches; the center part, designated "C" in FIG. 4, has preferred dimension of 5½ inches, the point to point dimension on the garment, designated "A" in FIG. 4, is preferably 8¾ inches; for the back of the crotch, designated "B" in FIG. 4, the dimension is 10".

The garment may be constructed in various ways without be constructed with a flap which is secured by VELCRO brand strips While this variation may be inappropriate for a ladies' garment, since it may detract from the overall sleekness of the garment, it may be particularly useful in a male undergarment of this type.

While the garment is primarily intended as an incontinent garment, as has already been mentioned, it may be used with an appropriate absorbent pad for women having their menstrual flow.

Again, while the garment has been designed for incontinent persons or typically older people, it may also be worn by children who are bed wetters or have difficulty retaining their urine.

While the foregoing description and drawings represent the preferred embodiments of the present invention, it will be obvious to those skilled in the art that various changes and modifications may be made therein without departing from the true spirit and scope of the present.

What is claimed is:

1. A re-usable garment to be worn on the lower part of the body for the retention of body fluids, comprising:
  a body portion of a breathable, elastic, fiber-containing material and a crotch portion; said body portion having a waist opening and said body portion and crotch portion forming leg openings, said crotch portion being sewn to said body portion; and
  said crotch portion being liquid-proof, breathable and elastic for the retention of body fluids and including a laminated fabric having a liquid-proof, breathable, elastic thermoplastic film inner layer and a breathable, stretch, fiber-containing material outer layer having substantial elastic qualities, said film of said film layer being a polymer film having a thickness less than 1.0 mil and having elastic qualities comparable to said stretch material; and an adhesive bonding said film layer to said layer of stretch material, said adhesive being present in substantially discontinuous segments; the material of said body portion and the material of said crotch portion outer layer being substantially similar so as to provide a uniform outer appearance of the garment similar to that of a conventional undergarment.

2. The garment of claim 1, wherein said stretch fiber-containing material layer is a knitted construction.

3. The garment of claim 1, including disposable shield means inserted in said crotch area, for absorption of body fluids.

4. The garment of claim 1, including elastic bands disposed along said leg openings for securing said leg openings against a leg when the garment is worn in order to prevent leakage of body fluids through said leg openings.

5. The garment of claim 1, wherein said body portion is an stretch fabric of knitted construction.

* * * * *